(12) United States Patent
Schiller

(10) Patent No.: US 9,930,733 B1
(45) Date of Patent: Mar. 27, 2018

(54) ELECTRODE JOINT SPACER

(71) Applicant: Contractors & Industrial Supply Company, Inc., Nashville, TN (US)

(72) Inventor: Tom D. Schiller, Franklin, TN (US)

(73) Assignee: Contractors & Industrial Supply Company, Inc., Nashville, TN (US)

( * ) Notice: Subject to any disclaimer, the term of this patent is extended or adjusted under 35 U.S.C. 154(b) by 463 days.

(21) Appl. No.: 14/693,652

(22) Filed: Apr. 22, 2015

Related U.S. Application Data

(60) Provisional application No. 61/982,337, filed on Apr. 22, 2014.

(51) Int. Cl.
*H05B 7/14* (2006.01)
*H05B 7/06* (2006.01)

(52) U.S. Cl.
CPC .................................... *H05B 7/14* (2013.01)

(58) Field of Classification Search
CPC . H05B 7/06; H05B 7/085; H05B 7/10; H05B 7/14; H05B 7/101; H05B 7/103; H05B 7/109
USPC ....... 373/51–53, 88, 91, 92, 94, 100; 285/93
See application file for complete search history.

(56) References Cited

U.S. PATENT DOCUMENTS

| 2,226,652 A | 12/1940 | York |
| 3,249,673 A | 5/1966 | Moore |
| 3,517,954 A | 6/1970 | Snyder et al. |
| 3,600,031 A | 8/1971 | Coleman et al. |
| 3,752,896 A | 8/1973 | Zimmermann et al. |
| 3,781,449 A | 12/1973 | Wolf et al. |
| 3,790,204 A | 2/1974 | Lighthipe, Jr. et al. |
| 3,796,818 A | 3/1974 | Yuasa et al. |
| 3,814,828 A | 6/1974 | Gazda |

(Continued)

FOREIGN PATENT DOCUMENTS

| IT | 1052996 B | 8/1981 |
| IT | 1192885 B | 5/1988 |

(Continued)

OTHER PUBLICATIONS

U.S. Appl. No. 14/693,673, filed Apr. 22, 2015, Schiller.

(Continued)

*Primary Examiner* — Hung D Nguyen
(74) *Attorney, Agent, or Firm* — Waller Lansden Dortch & Davis LLP; Matthew C. Cox

(57) ABSTRACT

An electrode joining apparatus for joining a free electrode to a fixed electrode. The electrode joining apparatus includes an electrode holder configured to selectively hold the fixed electrode and a torque device positioned above the electrode holder, the torque device configured to grip and spin the free electrode to join the electrodes. The electrode joining apparatus can include an axial passage defined through the electrode holder and the torque device. A retractable spacer can be movably connected to the electrode joining apparatus, the retractable spacer configured to selectively move into the axial passage. The retractable spacer can be used to form a gap between the free electrode and the fixed electrode before the joining process is initiated. Electrode joining apparatus can also include a spacer drive mechanism coupled to the retractable spacer, the spacer drive mechanism configured to selectively move the retractable spacer into the axial passage.

16 Claims, 14 Drawing Sheets

(56) References Cited

U.S. PATENT DOCUMENTS

| | | |
|---|---|---|
| 4,154,974 A | 5/1979 | Wynne |
| 4,162,368 A | 7/1979 | Brazier |
| 4,185,158 A | 1/1980 | Koga et al. |
| 4,317,951 A | 3/1982 | Boudeau et al. |
| 4,323,717 A | 4/1982 | Garner et al. |
| 4,349,910 A * | 9/1982 | Belz ............... H05B 7/14 373/92 |
| 4,400,815 A | 8/1983 | Dunn et al. |
| 4,420,838 A | 12/1983 | Dunn et al. |
| 4,665,530 A | 5/1987 | Corbethau |
| 4,703,492 A | 10/1987 | Sekiguchi et al. |
| 4,736,384 A | 4/1988 | Sakai et al. |
| 5,161,845 A | 11/1992 | Carpenter, Jr. |
| 5,208,442 A | 5/1993 | Ahola et al. |
| 5,255,285 A | 10/1993 | Abed et al. |
| 5,638,398 A | 6/1997 | Ikitsu et al. |
| 5,757,841 A | 5/1998 | Ikitsu et al. |
| 5,870,424 A | 2/1999 | Todoriki et al. |
| 6,084,200 A | 7/2000 | Ahola |
| 6,167,076 A | 12/2000 | Ignacio |
| 6,265,690 B1 | 7/2001 | Fornsel et al. |
| 7,547,861 B2 | 6/2009 | Jorgensen |
| 7,660,337 B2 | 2/2010 | Teeples et al. |
| 7,992,634 B2 | 8/2011 | Angelle et al. |
| 9,383,278 B1 | 7/2016 | Schiller |
| 2008/0084907 A1 | 4/2008 | Lehr et al. |
| 2010/0272146 A1 | 10/2010 | Piccardi |
| 2011/0089617 A1 | 4/2011 | Reali et al. |
| 2011/0274137 A9 | 11/2011 | Piccardi |
| 2015/0233195 A1 | 8/2015 | Smith et al. |

FOREIGN PATENT DOCUMENTS

| | | |
|---|---|---|
| IT | 1297835 A1 | 8/1998 |
| JP | 3388329 | 3/2003 |

OTHER PUBLICATIONS

U.S. Appl. No. 14/693,862, filed Apr. 22, 2015, Schiller.
U.S. Appl. No. 14/796,964, filed Jul. 10, 2015, Schiller.
U.S. Appl. No. 15/146,877, filed May 4, 2016, Schiller.
U.S. Appl. No. 15/198,949, filed Jun. 30, 2016, Schiller.

* cited by examiner

ELECTRODE JOINT SPACER

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application is a non-provisional of U.S. Provisional Patent Application Ser. No. 61/982,337 filed Apr. 22, 2014 entitled Electrode Joining Apparatus and Methods of which is herein incorporated by reference in its entirety.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to machinery for manipulating electrodes and more particularly to devices and methods for joining graphite electrodes for use with metal arc furnaces.

Metal arc furnaces include large vessels for melting metal. Heat may be generated inside the furnaces using graphite electrodes across which electric current is passed. Heat is generated inside the furnace due to a high voltage arc formed by the current passing through one or more electrodes. The heat is used to melt metal.

During use, graphite electrodes are consumed within the furnace vessel, requiring electrodes to be replaced over time. As electrode material is consumed in the furnace, the electrode is shortened to a length where it is no longer independently usable. However, a partially-consumed electrode may be joined to a second partially-consumed or complete electrode to form a joined electrode that can be used. Thus, the partially-consumed electrode may still be useful when placed in combination with a second electrode portion.

Electrodes may be joined in an end-to-end configuration using a threaded joint in some applications. When electrodes are combined, electrical conductivity is generally maintained across the joint, and electricity may be passed from one electrode to the second in the joint electrode. A threaded joint is commonly used to join electrodes. The joining procedure requires at least one electrode to be rotated relative to a second electrode such that a threaded engagement occurs.

The joining process typically requires two stages. During a first stage, the first or free electrode is rotated relative to the second or fixed electrode to allow loose engagement of the corresponding threads. Rotation during this stage encounters relatively little resistance as the threads are rotating. This may be referred to as a spin-down rotation when a free electrode is spun about its longitudinal axis relative to a fixed electrode below the free electrode, to allow the threads to engage. In the second stage, or torque phase, an increase torque force is applied to the free electrode to tighten the free electrode to a manufacturer's suggested torque value.

Conventional tools and methods for joining electrodes in a threaded joint include powered electrode joining devices including an electrode holder that is configured to grip the fixed electrode, and a torque device that is configured to grip and spin the free electrode on the fixed electrode.

It is generally desirable to introduce the lower end of the free electrode into the electrode joining device at a specific distance above the upper end of the fixed electrode before the initial spin down occurs. The gap between the free electrode and the fixed electrode can help prevent damage to the threads on the electrodes as the free electrode is lowered down into the electrode joining device. Conventional techniques for setting the gap include manually placing a gap spacer on the upper end of the fixed electrode, lowering the free electrode until the free electrode meets the spacer, and then manually removing the spacer. Such a procedure is burdensome on workers and requires a worker to be near the joining zone, which can be unsafe.

What is needed then are improvements in electrode joint spacer apparatuses.

BRIEF SUMMARY

One aspect of the present disclosure is an electrode joining apparatus for joining a free electrode to a fixed electrode. The electrode joining apparatus can include an electrode holder configured to selectively hold the fixed electrode, and a torque device positioned above the electrode holder, the torque device configured to grip and spin the free electrode to join the free electrode to the fixed electrode. The electrode joining apparatus can include an axial passage defined through the electrode holder and the torque device. A retractable spacer can be movably connected to the electrode joining apparatus, the retractable spacer configured to selectively move into the axial passage. The retractable spacer can be used to form a gap between the free electrode and the fixed electrode before the joining process is initiated.

In some embodiments, the electrode joining apparatus can also include a spacer drive mechanism coupled to the retractable spacer, the spacer drive mechanism configured to selectively move the retractable spacer into the axial passage. The spacer drive mechanism in some embodiments can be a hydraulic, a pneumatic, or an electric actuator.

In some embodiments, the retractable spacer can be pivotally connected to the electrode joining apparatus. In other embodiments, the retractable spacer can be configured to advance radially with respect to the electrode joining apparatus to move into the axial passage. In some embodiments the retractable spacer can be positioned between the electrode holder and the torque device. In other embodiments the retractable spacer can be movably connected to either the electrode holder or the torque device.

One objective of the present disclosure is to provide a spacer which can be used to set an initial gap between a fixed electrode and a free electrode being joined together.

Another objective is to help alleviate the need for an operator to be near the joint zone of two electrodes during the joining process.

Another objective is to provide a powered, actuated, or driven retractable spacer.

Numerous other objects, advantages and features of the present disclosure will be readily apparent to those of skill in the art upon a review of the following drawings and description.

DETAILED DESCRIPTION

Figure 1:
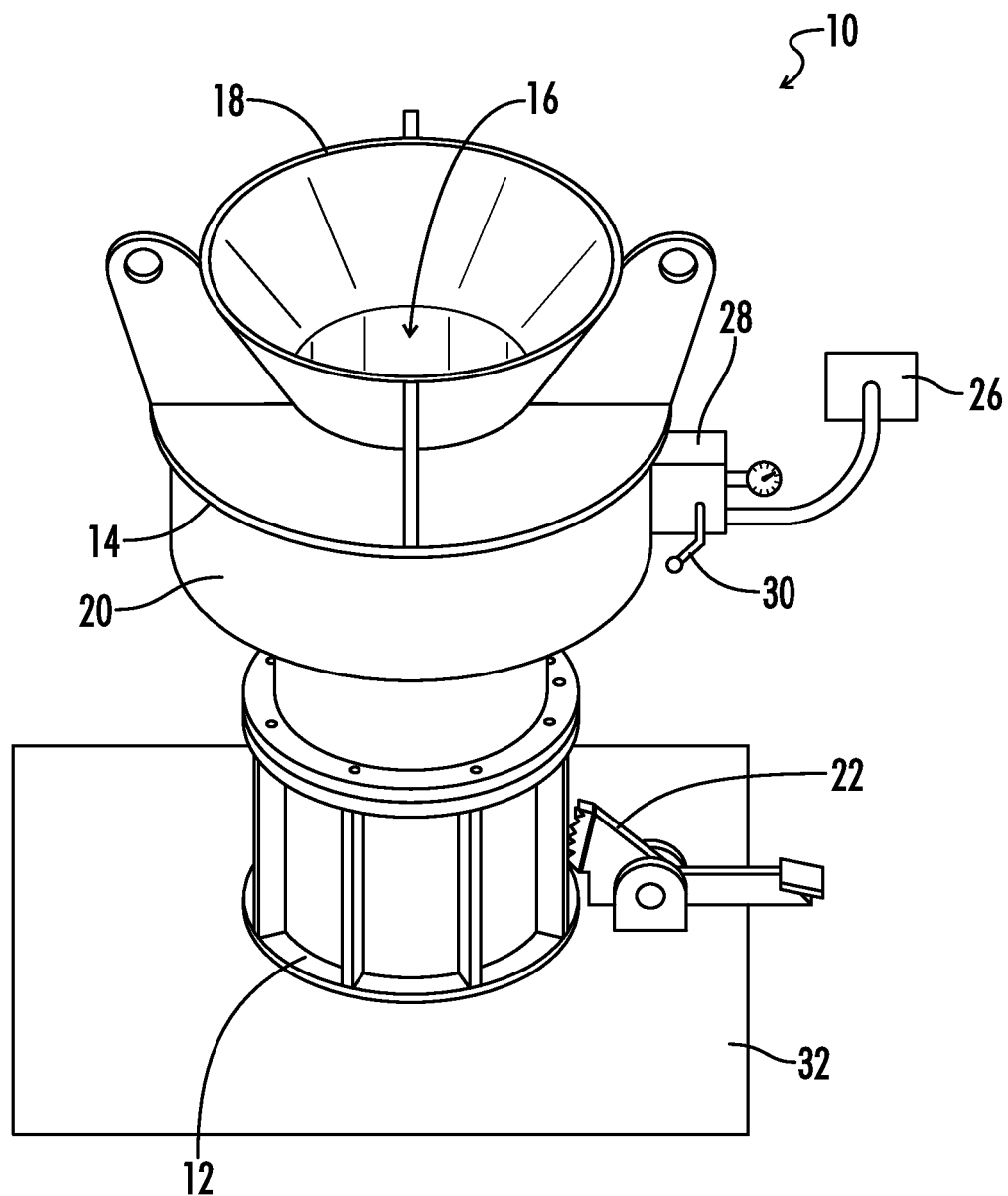
FIG. 1 is a perspective view of an embodiment of an electrode joining apparatus.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

As described herein, an upright position is considered to be the position of apparatus components while in proper operation or in a natural resting position as described herein. Vertical, horizontal, above, below, side, top, bottom and other orientation terms are described with respect to this upright position during operation unless otherwise specified. The term "when" is used to specify orientation for relative positions of components, not as a temporal limitation of the claims or apparatus described and claimed herein unless otherwise specified. The term "lateral" denotes a side to side direction when facing the "front" of an object.

The phrase "in one embodiment," as used herein does not necessarily refer to the same embodiment, although it may. Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the apparatuses and/or methods disclosed and claimed herein may be made and/or executed without undue experimentation in light of the present disclosure. While the apparatuses and methods of this invention have been described in terms of the embodiments included herein, it will be apparent to those of ordinary skill in the art that variations may be applied to the apparatuses and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Referring now to the drawings, an embodiment of an electrode joining apparatus 10 is shown in FIG. 1. Electrode joining apparatus 10 can include electrode holder 12 and torque device 14. An axial passage 16 can extend through electrode holder 12 and torque device 14, axial passage 16 allowing passage of one or more electrodes through electrode joining apparatus 10. In some embodiments, torque device 14 can include an upper funnel 18 which can facilitate centering of an electrode being lowered into electrode joining apparatus 10 through axial passage 16.

In some applications, graphite electrodes can be joined in an end to end fashion using a threaded joint. Joining the electrodes requires one electrode to be rotated relative to the other electrode. In such applications, a fixed electrode can be received and held by electrode holder 12 and torque device 14 can be configured to grip and spin a free electrode down onto the fixed electrode to effectively join the two electrodes together. Electrode holder 12 can include a holder grip 22 which can be rotated to selectively fix or clamp an electrode within electrode holder 12. In some embodiments, electrode holder 12 can be configured to prevent rotational or axial movement of an electrode once the holder grip 22 engages the electrode. Electrode holder 12 can be securely fixed to a platform 32 on which operators can work.

In some embodiments, torque device 14 can include machinery which can rotate a free electrode lowered through funnel 18 into torque device 14. The machinery can be contained in housing 20. The machinery can generally grip the lower end of the free electrode and apply a rotational force to the free electrode. In some embodiments, the machinery can include a plurality of gripper pawls that are connected to a gear system which is rotated by a drive motor. The machinery can apply rotational force to the free electrode during both the spin down and torque stages, or in some embodiments the machinery can be configured to apply rotational force to the free electrode only during the torque stage. In some embodiments, the machinery can be powered by a mechanical actuator 26 such as a hydraulic pressure system, or a pneumatic pressure system. In other embodiments the drive motor for torque device 14 can be powered electrically. In other embodiments the machinery can be powered manually. In some embodiments, torque device 14 can include control console 28. Control console 28 can include lever 30 which can be used to control the supply of input such as hydraulic or pneumatic pressure or mechanical force to torque device 14.

In other embodiments, control console 28 can be placed in a separate location such as a control room or other remote location and torque device 14 can be operated without an operator being present near electrode joining apparatus 10. In some embodiments, control console 28 can be electrically connected to torque device 14, while in other embodiments control console 28 can communicate with torque device 14 through wireless telemetry.

It is generally desirable to set a gap between the free electrode and the fixed electrode before the spin down stage and before the torque device begins rotating such that the corresponding threads on a fixed electrode and a free electrode can engage each other gradually which can help prevent damage to the threads or to the electrodes themselves. In conventional electrode joining apparatuses, an operator had to place a spacer between the electrodes manually, which could be dangerous as the operator was present in the joining zone.

Figure 2:
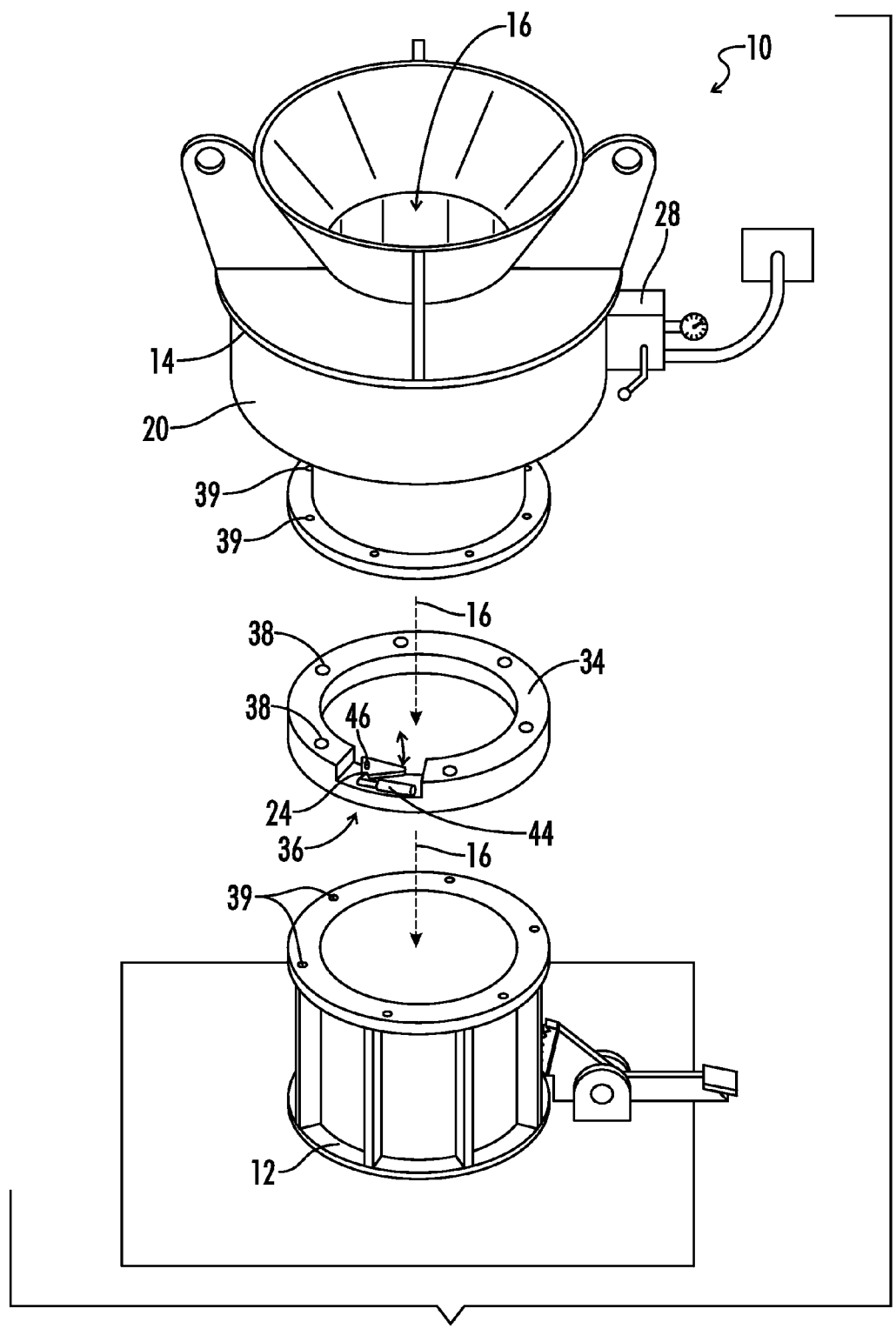
FIG. 2 is an exploded perspective view of an electrode joining apparatus including a retractable spacer positioned between a torque device and an electrode holder.
Figure 3:
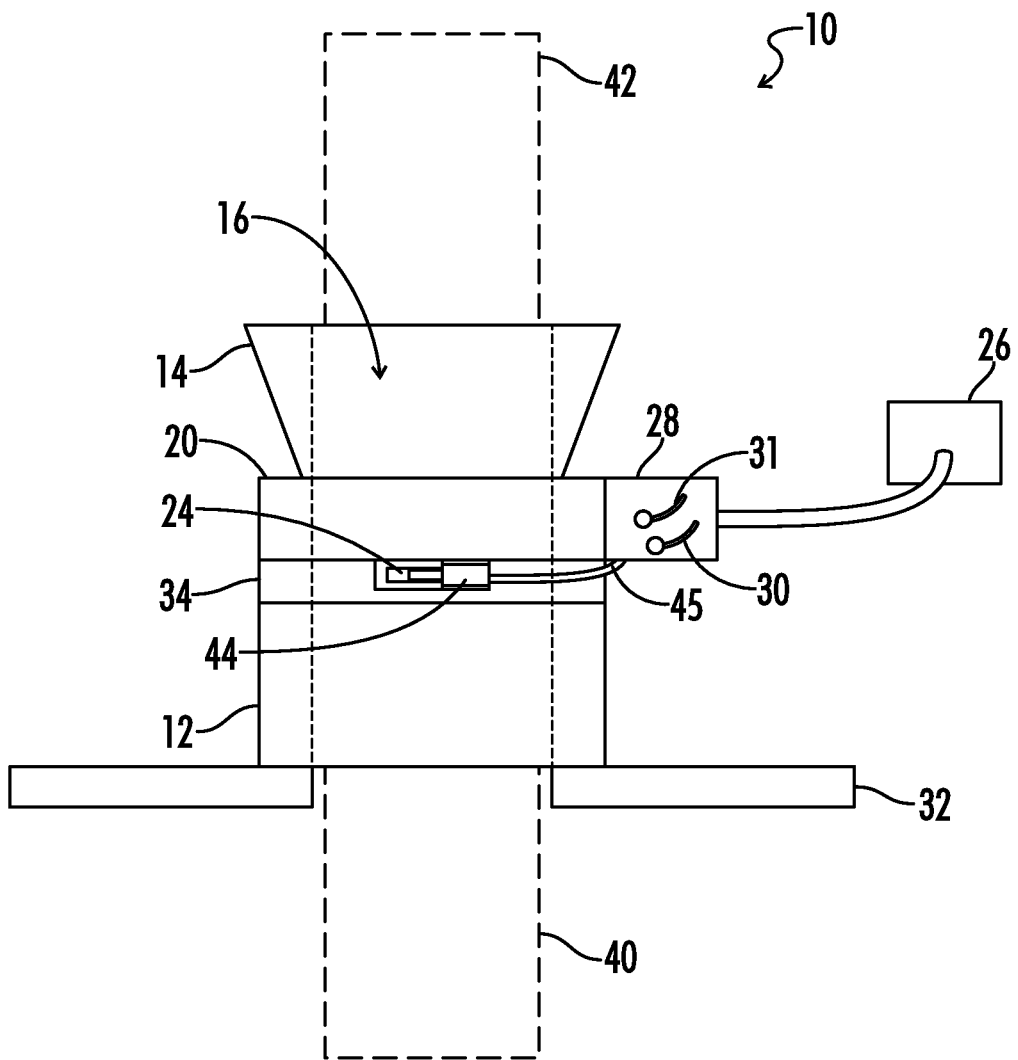
FIG. 3 is an side view of the assembled electrode joining apparatus of FIG. 2.

An embodiment of an electrode joining apparatus 10 including a retractable spacer 24 is shown in FIG. 2 and FIG. 3. Retractable spacer 24 can be movably connected to electrode joining apparatus 10, and retractable spacer 24 can be configured to selectively move into axial passage 16. As such, retractable spacer 24 can be moved into axial passage 16 as desired when an operator desires to set a gap between a fixed electrode and a free electrode which can be positioned in the electrode joining apparatus 10. With retractable spacer 24 extending into axial passage 16, a fixed electrode can be positioned against the bottom of retractable spacer 24 and a free electrode can be positioned against the top of retractable spacer 24 in order to form a gap between the fixed electrode and the free electrode. Once the gap is set, retractable spacer 24 can be retracted such that the spin down stage of the joining procedure can be initiated.

Figure 16:
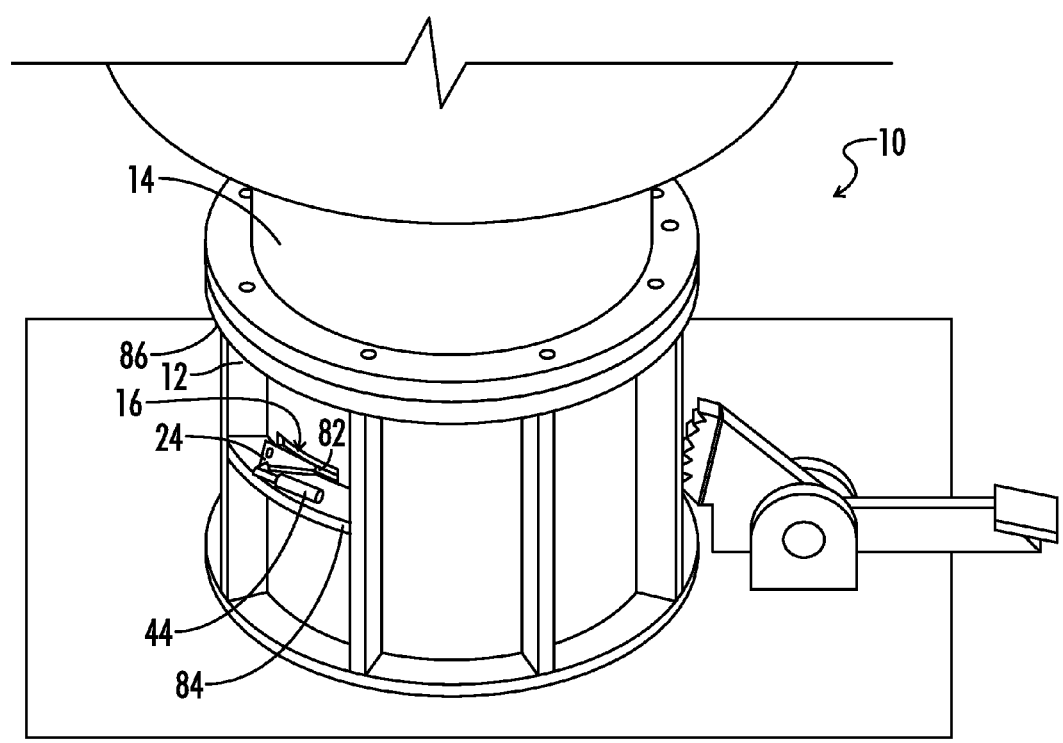
FIG. 16 is a perspective view of another embodiment of an electrode joining apparatus having a retractable spacer pivotally connected to an electrode holder.

In some embodiments, as shown in FIG. 2, retractable spacer 24 can be positioned between torque device 14 and electrode holder 12. In other embodiments, as shown in FIG. 16, retractable spacer 24 can be movably connected to electrode holder 12. Electrode holder 12 can include a spacer window 82 which can allow retractable spacer 24 to pass into axial passage 16. Retractable spacer 24 can be positioned on a spacer platform 84 positioned adjacent spacer window 82. In other embodiments, retractable spacer 24 may be movably connected to a top flange 86 of electrode holder 12.

Figure 17:
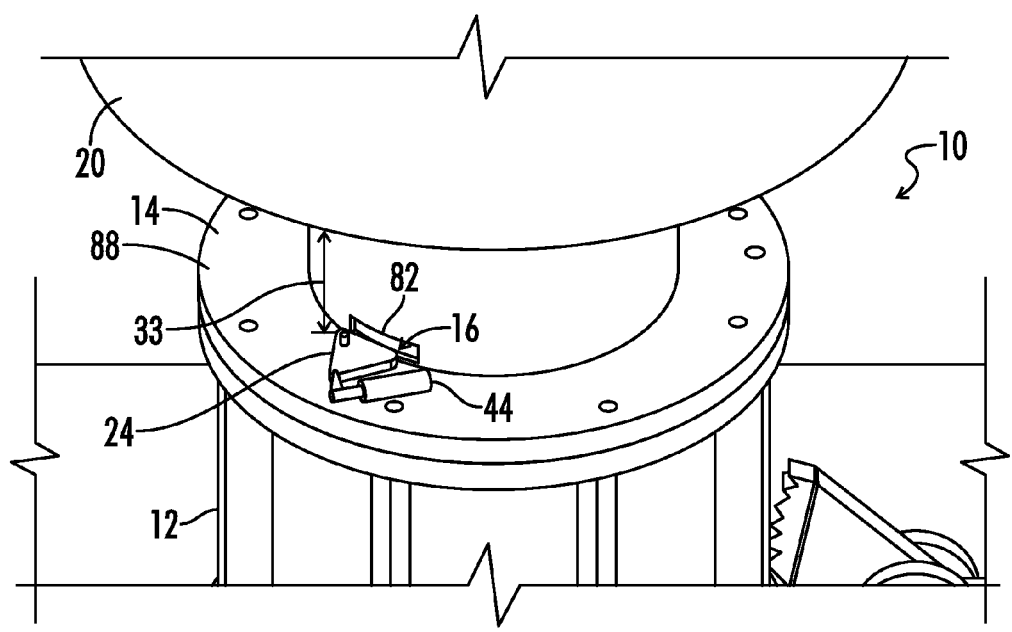
FIG. 17 is a perspective view of another embodiment of an electrode joining apparatus having a retractable spacer pivotally connected to a torque device.

In still other embodiments, as shown in FIG. 17, retractable spacer 24 can be movably connected to torque device 14. In such embodiments, spacer window 82 can be defined in torque device 14 to allow retractable spacer 24 to pass into axial passage 16. In some embodiments, retractable spacer 24 can be movably connected to a lower flange 88 of torque device 14.

Generally speaking, retractable spacer 24 can be positioned below torque device machinery contained in housing 20 on torque device 14. The torque device machinery can be configured the apply a torque on a free electrode being joined to a fixed electrode in order to grip and spin the free electrode onto the fixed electrode. As such, retractable spacer 24 can be positioned below the torque device machinery such that when a free electrode engages retractable spacer 24 to set a gap between the free electrode and a fixed electrode, the torque device machinery can be in a position to engage the free electrode.

In some embodiments, retractable spacer 24 can be positioned at an offset distance 33 below the torque device machinery contained in housing 20 such that when a free electrode engages retractable spacer 24, the torque device machinery engages the free electrode at an engagement point located a predetermined distance above retractable spacer 24 and the lower end of the free electrode. The torque device machinery engaging the free electrode at an engagement point above the lower end of the free electrode can help provide a more stable engagement between torque device 14 and the free electrode, as well as a more stable and balanced spin down of the free electrode. In some embodiments, offset distance 33 between retractable spacer 24 and the torque device machinery can be greater than or equal to about 12 inches.

In some embodiments, as shown in FIG. 2, electrode joining apparatus 10 can include a spacer support structure 34, and retractable spacer 24 can be connected to spacer support structure 34. In some embodiments, spacer support structure 34 can be positioned between torque device 14 and electrode holder 12, and spacer support structure 34 can be configured to support the weight of torque device 14. Spacer support structure 34 can be configured to allow retractable spacer 24 to selectively move into axial passage 16. In some embodiments, spacer support structure 34 can be a support ring or flange which includes a radial slot 36 in which retractable spacer 24 can be positioned.

In a conventional electrode joining apparatus, electrode holder 12 and torque device 14 can be bolted together, as shown in FIG. 1. As such, in some embodiments an existing electrode joining apparatus 10 can be retrofitted with a retractable spacer 24 by unbolting torque device 14 and electrode holder 12 and positioned spacer support structure 34 and retractable spacer 24 between torque device 14 and electrode holder 12, as shown in FIG. 2. In some embodiments, spacer support structure 34 can include one or more bolt holes 38 which can be aligned with existing bolt holes 39 in torque device 14 and electrode holder 12, such that spacer support structure 34 can be connected to electrode holder 12 and torque device 14 via bolt holes 38 without having to alter either electrode holder 12 or torque device 14.

Figure 4:
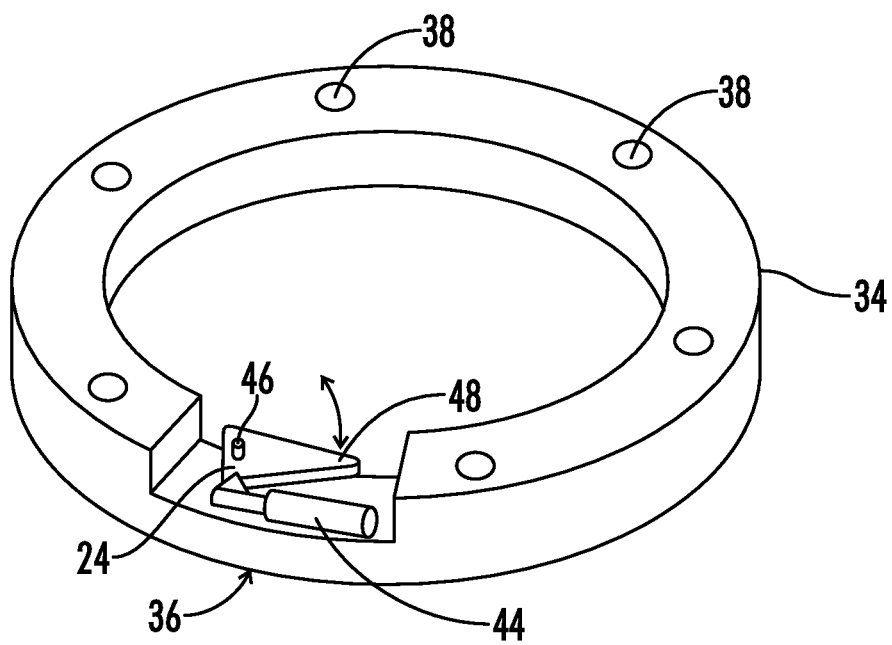
FIG. 4 is a perspective view of an embodiment of a retractable spacer insert for an electrode joining apparatus.

One embodiment of a spacer support structure 34 with a movably connected retractable spacer 24 is shown in FIG. 4. Retractable spacer 24 can be pivotally connected to spacer support structure 34 such that when spacer support structure 34 is connected to an electrode joining apparatus 10 as shown in FIG. 2 and FIG. 3, retractable spacer 24 can be configured to pivot with respect to electrode joining apparatus 10 such that retractable spacer 24 can selectively move into axial passage 16.

Figure 5:
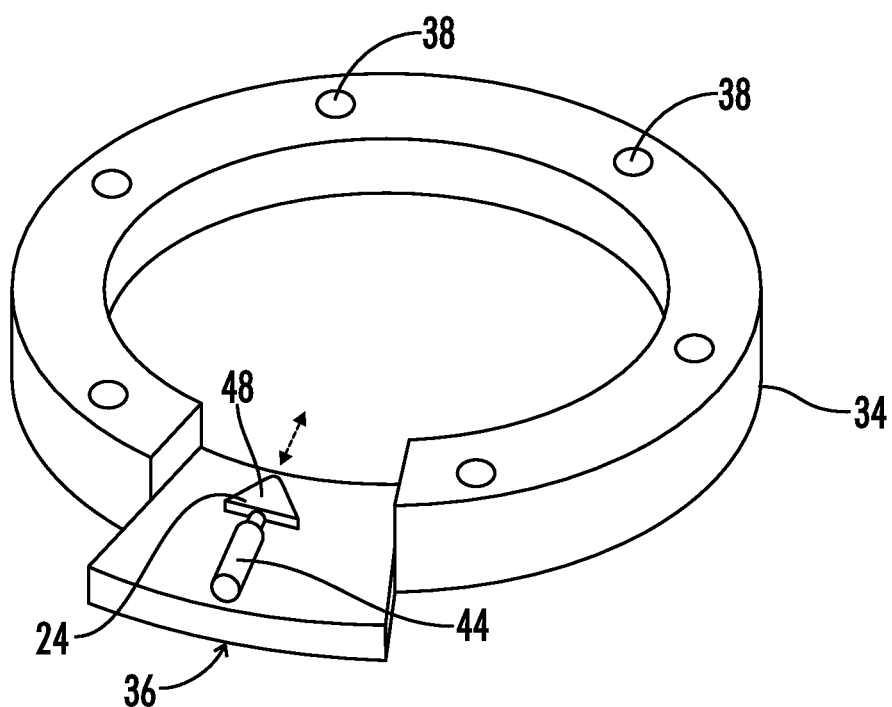
FIG. 5 is a perspective view of another embodiment of a retractable spacer insert for an electrode joining apparatus.

Another embodiment of a spacer support structure 34 with a movably connected retractable spacer 24 is shown in FIG. 5. Retractable spacer 24 can be connected to spacer support structure 34 such that retractable spacer 24 can move radially with respect to spacer support structure 34. As such, when spacer support structure 34 is connected to an electrode joining apparatus, retractable spacer 24 can advance radially with respect to the electrode joining apparatus in order for retractable spacer 24 to selectively move into an axial passage of the electrode joining apparatus.

In some embodiments, as seen in FIGS. 2-5, a spacer drive mechanism 44 can be coupled to retractable spacer 24. Spacer drive mechanism 44 can be configured to selectively move retractable spacer 24 into axial passage 16. Spacer drive mechanism 44 can be mounted to electrode joining apparatus 10, and in some embodiments can be mounted to spacer support structure 34. In some embodiments, spacer drive mechanism 44 can be a hydraulic actuator. In other embodiments, spacer drive mechanism 44 can be a pneumatic actuator. In still other embodiments, spacer drive mechanism 44 can be a mechanical actuator such as an electric motor configured to move retractable spacer 24. In some embodiments, spacer drive mechanism 44 can be powered by the same input as torque device 14, and control console 28 can be configured to control the supply of actuation input to spacer drive mechanism 44. For instance, if torque device 14 is powered hydraulically, a hydraulic line 45 can run from the torque device control console 28 to the spacer drive mechanism 44, as shown in FIG. 3. In embodiments where torque device 14 is powered pneumatically, a pneumatic line can be run from control console 28 to spacer drive mechanism 44. In other embodiments, spacer drive mechanism 44 can be powered by a separate input from torque device 14, such as a separate hydraulic pump or a compressed gas tank coupled to a compressor.

In some embodiments, control console 28 mounted to torque device 14 can include a torque device control. Control console 28 can also include a spacer control which can be operated independently of the torque device control. The spacer control can be communicated with spacer drive mechanism 44 to control the actuation of spacer drive mechanism 44 in order to alternate retractable spacer 24 between a retracted and an extended position. In one embodiment, torque device 14 and retractable spacer 24 can be controlled using a single lever 30 on control console 38. In such an embodiment, lever 30 can be moved along a first axis to control torque device 14, and lever 30 can be operated along a second axis to control retractable spacer 24. In other embodiments, as shown in FIG. 3, a first lever 30 on the control console 28 can control torque device 14 and a second lever 31 on control console 28 can control retractable spacer 24. As such, an operator does not have to manually set retractable spacer 24 in place between a fixed and free electrode, and the operator can control the position of retractable spacer 24 from control console 28 away from the joint zone.

Spacer drive mechanism 44 in some embodiments can be coupled to a valve which can be selectively opened in order to supply an actuation input to spacer drive mechanism. As such, the valve can cause spacer drive mechanism 44 to selectively move retractable spacer 24 into axial passage 16. Control console 28 can be configured to control the valve. In embodiments where control console 28 is remote from torque device 14, both torque device 14 and the valve selectively supplying actuation input to spacer drive mechanism 44 can be controlled using wireless telemetry from the remotely situated control console.

In some embodiments, electrode joining apparatus 10 can be an off-furnace type electrode joining apparatus 10, with a fixed electrode being removed from a furnace and placed in electrode joining apparatus 10, electrode joining apparatus being separated from the furnace. In other embodiments, electrode joining apparatus 10 can be an on-furnace type electrode joining apparatus 10, where a free electrode is joined to a fixed electrode while the fixed electrode is still disposed in the furnace.

In embodiments where retractable spacer 24 can pivot with respect to an electrode joining apparatus, spacer drive mechanism 44 can be any suitable mechanism which can cause retractable spacer 24 to rotate and selectively move into an axial passage of the electrode joining apparatus. For instance, in FIG. 4 spacer drive mechanism 44 is a hydraulic or pneumatic actuator cylinder which is connected to a corner of retractable spacer 44. As spacer drive mechanism 44 is actuated, spacer driver mechanism 44 cause the corner of retractable spacer 44 to rotate about pivot point 46, thereby causing distal end 48 of retractable spacer 24 to extend into an axial passage of the electrode joining apparatus.

In some embodiments, a retractable spacer can include a gear portion, and a spacer drive mechanism can include a corresponding gear portion configured to mesh with the gear portion on the retractable spacer. The spacer drive mechanism can be configured to move the corresponding gear portion, either rotationally or linearly, to cause retractable spacer to rotate via the gear portion on the retractable spacer such that the retractable spacer extends into an axial passage of an electrode joining apparatus.

In embodiments where retractable spacer 24 is configured to selectively advance radially with respect to an electrode joining apparatus, spacer drive mechanism 44 can be any suitable mechanism which when actuated can cause retractable spacer 24 to advance radially and selectively move into an axial passage of the electrode joining apparatus. For instance, in FIG. 5 spacer drive mechanism 44 can be a hydraulic or pneumatic actuator cylinder which can be oriented to move retractable spacer 24 radially with respect to the electrode joining apparatus when actuated in order to move distal end 48 of retractable spacer 24 into an axial passage of the electrode joining apparatus.

In other embodiments, a spacer drive mechanism can include a linear stage configured to move radially with respect to an electrode joining apparatus, and retractable spacer 24 can be positioned on the linear stage such that retractable spacer 24 can selectively move into an axial passage of the electrode joining apparatus when the linear stage is actuated. The spacer drive mechanism can include a hydraulic or pneumatic actuator configured to move the linear stage, or the linear stage can be powered by an electric motor.

Figure 6:
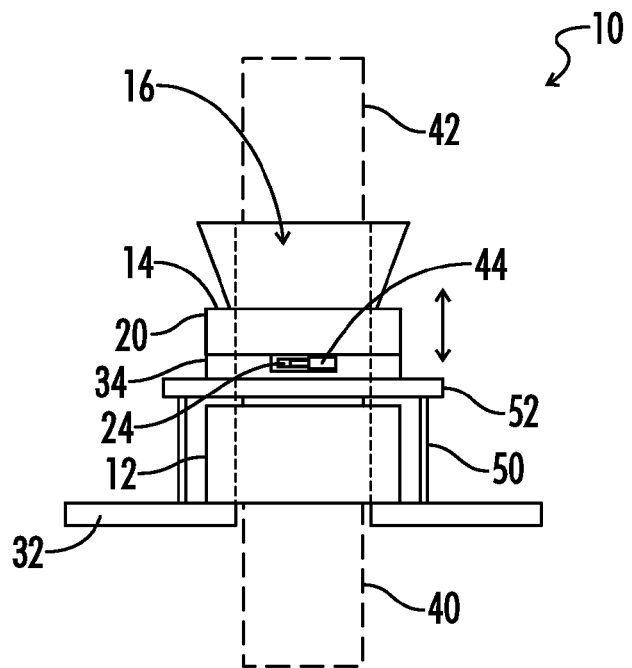
FIG. 6 is a side view of an embodiment of an electrode joining apparatus having a retractable spacer and a lift configured to vary the vertical position of a torque device of the electrode joining apparatus.
Figure 7:
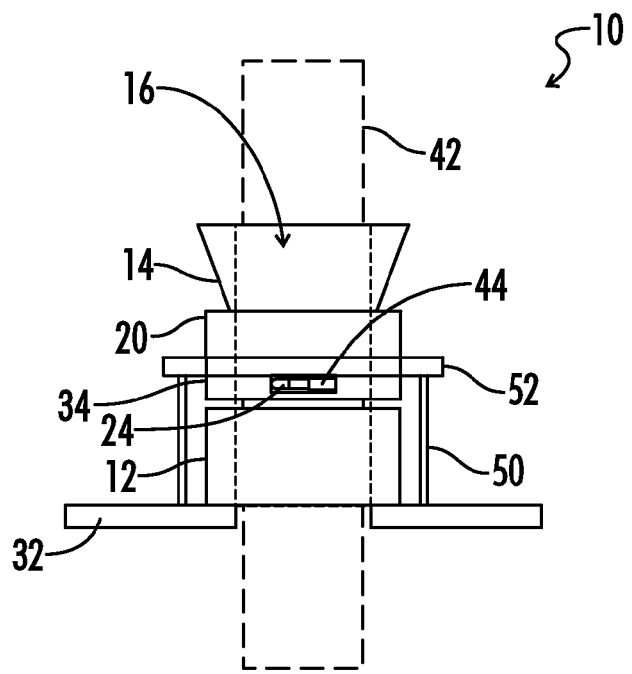
FIG. 7 is a side view of another embodiment of an electrode joining apparatus including a lift and a retractable spacer positioned below the lift.

In some embodiments, as shown in FIGS. 6 and 7, electrode joining apparatus 10 can include a lift 50. Lift 50 can be configured to vary the vertical position of torque device 14. In some electrode joining procedures, when a used or fixed electrode 40 is lowered into electrode joining apparatus 10, the dimensions of an electrode carrier on a crane may limit the distance the used electrode can be lowered into electrode joining apparatus 10 such that the top of the used electrode is positioned above torque device 14. It may then be necessary to raise torque device 14 such that torque device 14 can engage a free electrode 42 positioned above the used or fixed electrode 40.

Lift 50 may include carriage 52 on which torque device 14 can be positioned. Lift 50 can then move carriage 52 vertically to vary the position of torque device 14 as necessary. Lift 50 can include any suitable mechanism for lifting torque device 14 via carriage 52, including a hydraulic, pneumatic, or electric lift mechanism. In embodiments including a lift 50, retractable spacer 24 or spacer support structure 34 can be connected to lift 50 via carriage 52. In some embodiments retractable spacer 24 can be positioned between torque device 14 and carriage 52 as shown in FIG. 6. In other embodiments retractable spacer 24 can be positioned below carriage 52 with spacer support structure 34 and retractable spacer 24 suspended below carriage 52, as shown in FIG. 7.

Figure 8A:
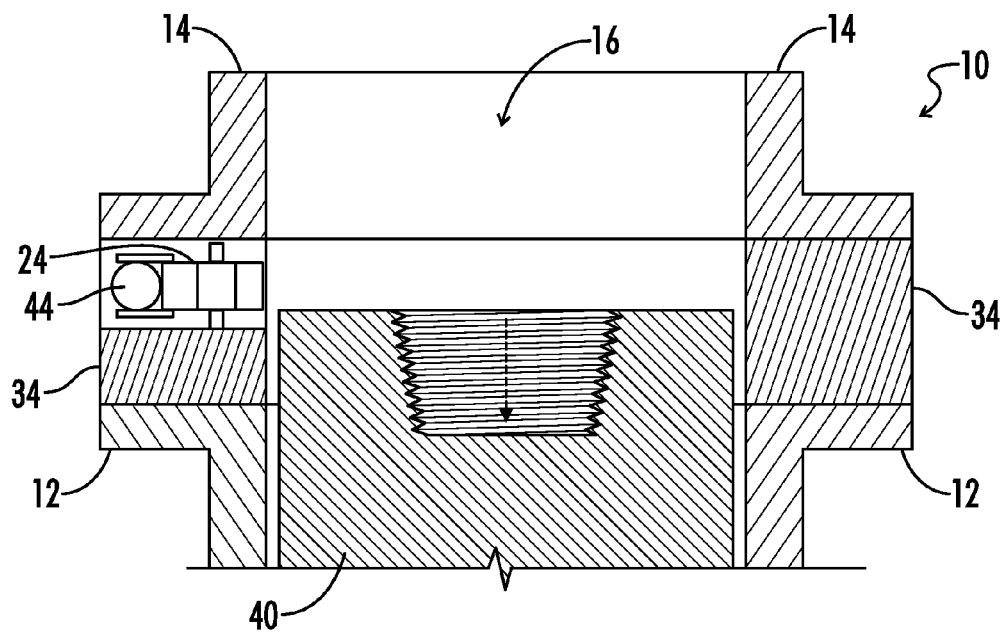
FIG. 8A is a cross section view of the electrode joining apparatus of FIG. 3 showing the retractable spacer in a retracted position and a fixed electrode being positioned in the electrode joining apparatus below the retractable spacer.
Figure 8B:
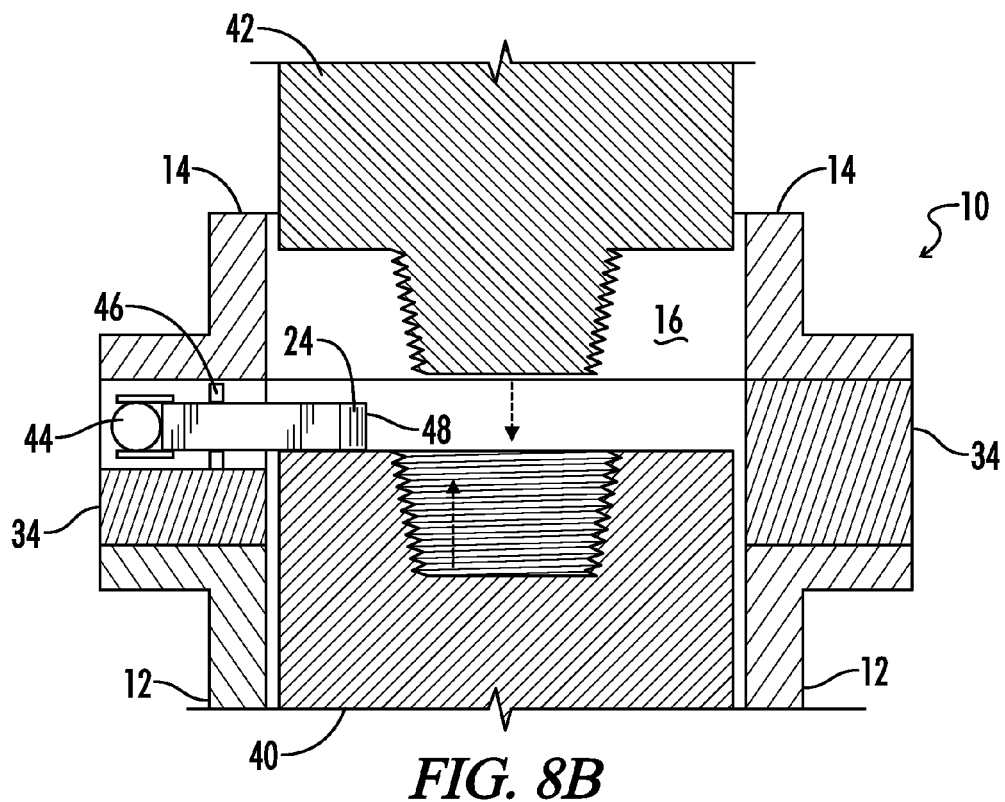
FIG. 8B is a cross section view of the electrode joining apparatus of FIG. 8A showing the retractable spacer extending into an axial passage and a free electrode being lowered into the electrode joining apparatus.

A method of setting a gap between a fixed electrode and a free electrode before an electrode joining apparatus spin down stage is shown in FIGS. 8A-8D. With retractable spacer 24 in a retracted position on spacer support structure 34 between torque device 14 and electrode holder 12, a fixed electrode 40 can be lowered into axial passage 16 of electrode joining apparatus 10. Fixed electrode 40 can initially be placed vertically below retractable spacer 24 as shown in FIG. 8A. Spacer drive mechanism 44 can then be actuated to move retractable spacer 24 into axial passage 16. In FIG. 8B, retractable spacer 24 is rotated by spacer drive mechanism 44 about pivot point 46 to move retractable spacer 24 into axial passage 16. In other embodiments, retractable spacer 24 can advance radially into axial passage 16.

Figure 8C:
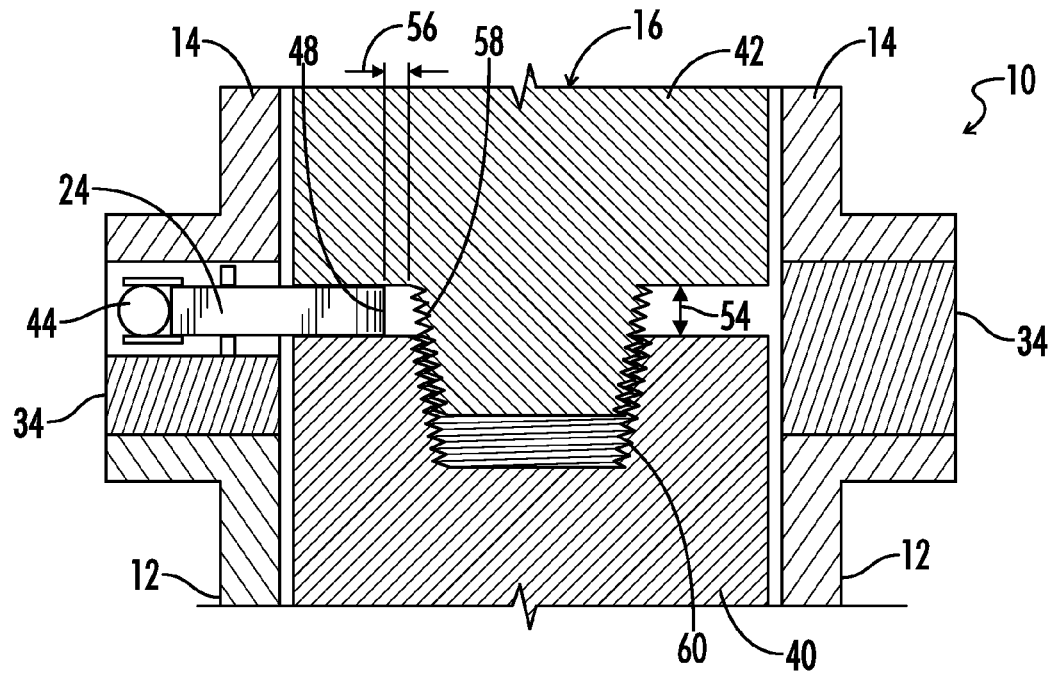
FIG. 8C is a cross section view of the electrode joining apparatus of FIG. 8C with the free electrode abutting the retractable spacer.

With retractable spacer 24 extending into axial passage 16, fixed electrode 40 can then be raised until fixed electrode 40 engages the bottom of retractable spacer 24. Electrode holder 12 can then engage fixed electrode 40 to retain the vertical position of fixed electrode 40. A free electrode 42 can then be lowered into axial passage 16. As shown in FIG. 8C, free electrode 42 can be lowered until free electrode 42 engages the top of retractable spacer 24. As such, a gap 54 can be set between fixed electrode 40 and free electrode 42.

In some embodiments, retractable spacer 24 can be configured such that when free electrode 42 is lowered onto retractable spacer 24, there is an offset distance 56 formed between distal end 48 of retractable spacer 24 and threads 58 on free electrode 42. The offset distance 56 can help prevent damage to threads 58 from retractable spacer 24 as free electrode 42 is lowered onto retractable spacer 24.

Figure 8D:
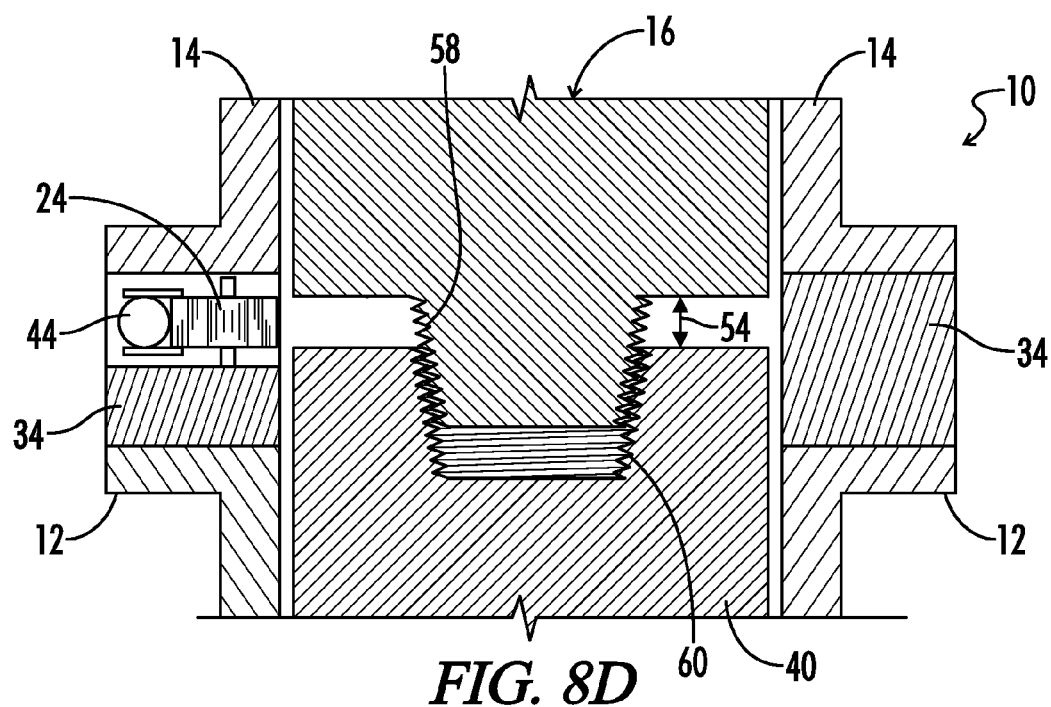
FIG. 8D is a cross section view of the electrode joining apparatus of FIG. 8C showing the retractable spacer moved back to a retracted position before the spin down stage commences.

Free electrode 42 can subsequently be raised just enough for the weight of free electrode 42 to be removed from retractable spacer 42. Spacer driver mechanism 44 can then be actuated again to move retractable spacer 24 back into a retracted position on spacer support structure 34, with gap 54 retained between fixed electrode 40 and free electrode 42, as shown in FIG. 8D. With retractable spacer 24 in a retracted position, torque device 14 can engage free electrode 42 to begin the spin down process such that threads 58 on free electrode 42 can engage corresponding threads 60 on fixed electrode 40 to tighten the two electrodes together.

Figure 9:
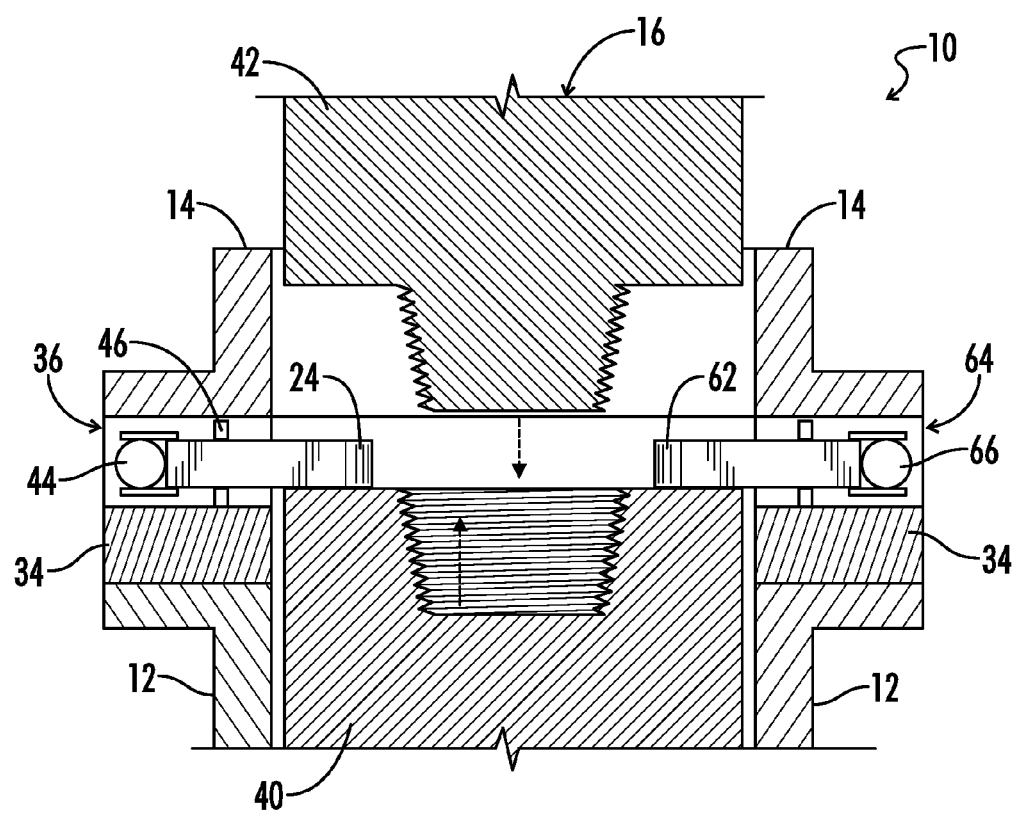
FIG. 9 is a cross section view of another embodiment of an electrode joining apparatus having a plurality of retractable spacers.
Figure 10:
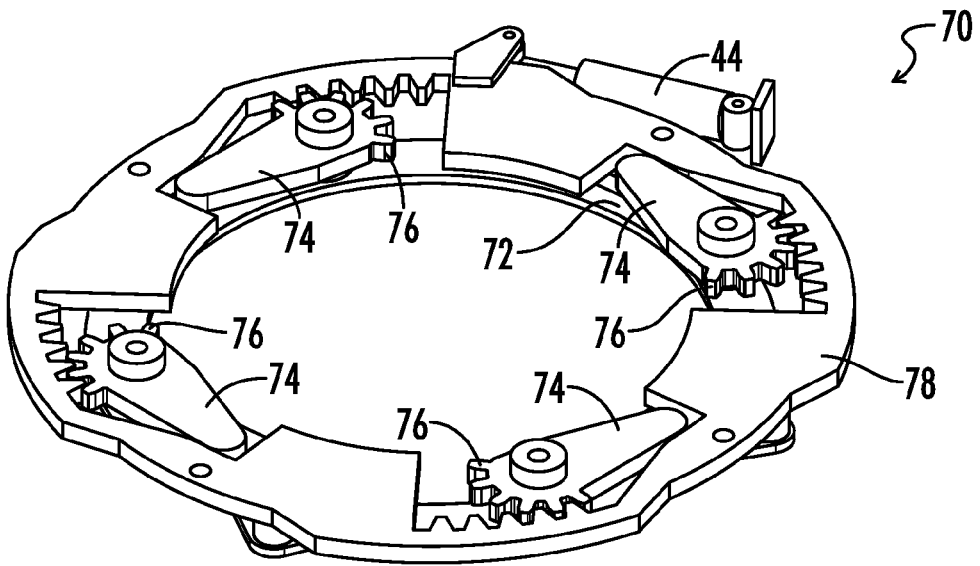
FIG. 10 is a perspective view of a gear system which can be mounted to an electrode joining apparatus, the gear system including a plurality of retractable spacers in a retracted position.
Figure 11:
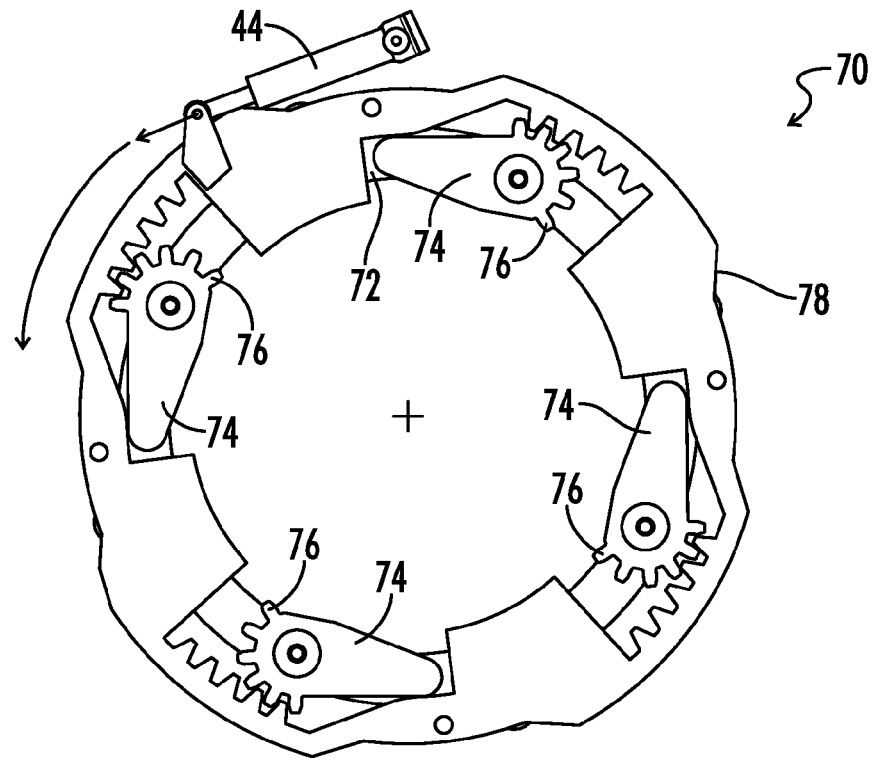
FIG. 11 is a top view of the gear system of FIG. 10.
Figure 12:
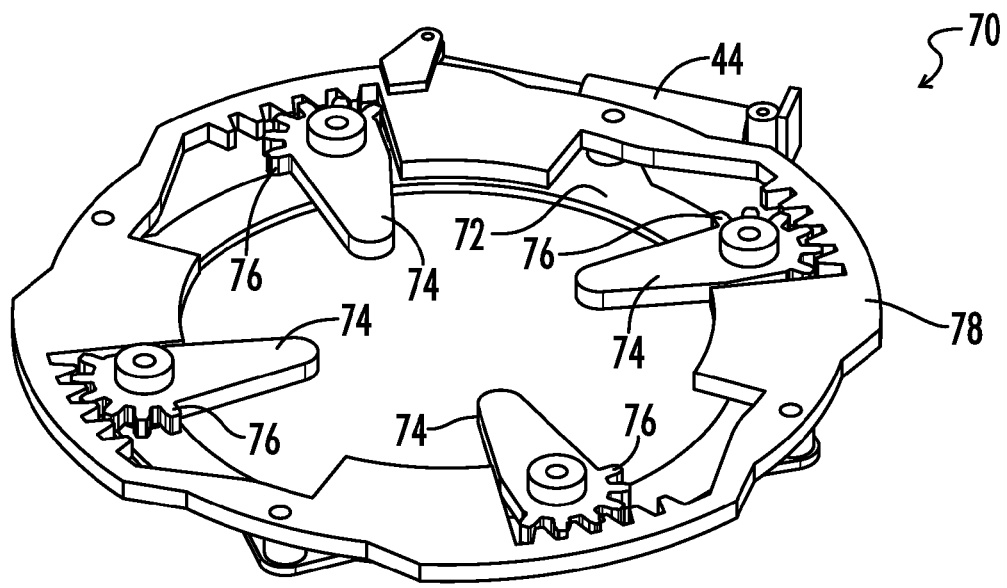
FIG. 12 is a perspective view of the gear system of FIG. 10 with the retractable spacers in an extended position.
Figure 13:
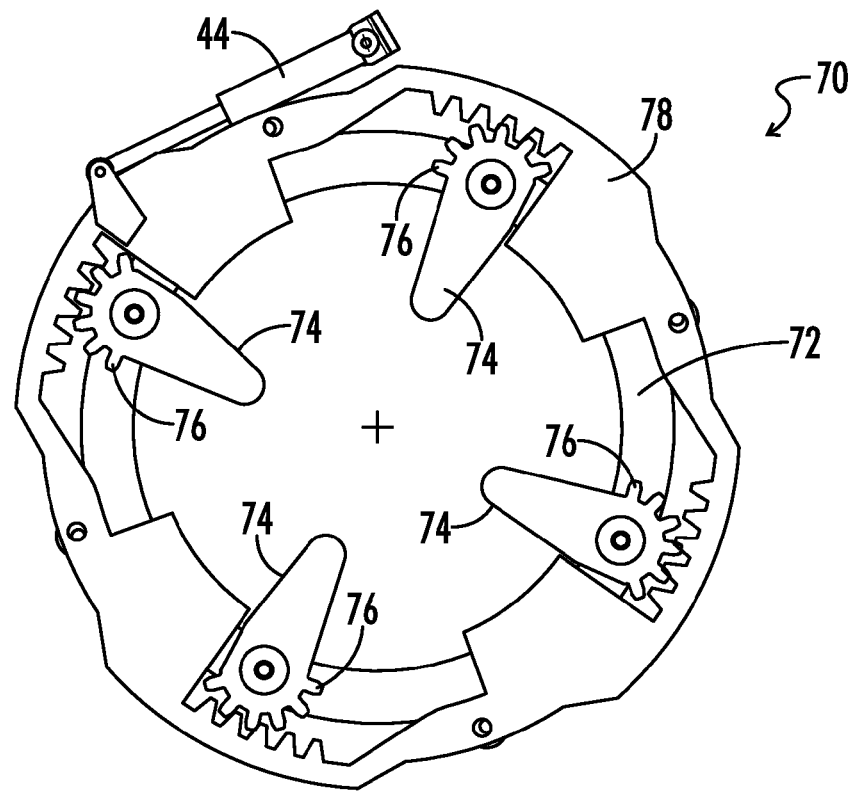
FIG. 13 is a top view of the gear system of FIG. 12.

Another embodiment of an electrode joining apparatus 10 having a second retractable spacer 62 movably connected to electrode joining apparatus 10 is shown in FIG. 9. Second retractable spacer 62 can be configured to selectively move into axial passage 16. Second retractable spacer 62 can have any of the orientations previously described for retractable spacer 24. Retractable spacer 24 and second retractable spacer 62 can generally be positioned opposite one another on electrode joining apparatus 10. As such, as a free electrode 42 is lowered into axial passage 16, free electrode 16 can engage both retractable spacers 24 and 62 on either side of axial passage 16 which can help keep free electrode 42 balanced and oriented vertically within axial passage 16.

In some embodiments, both retractable spacers 24 and 62 can be connected to spacer support structure 34 which can be connected between torque device 14 and electrode holder 12. Spacer support structure 34 can include a second radial slot 64 in which second retractable spacer 62 can be positioned. Electrode joining apparatus 10 can also include in some embodiments, as shown in FIG. 9, a second spacer drive mechanism 66 coupled to second retractable spacer 62. Second spacer drive mechanism 66 can be configured to selectively move second retractable spacer 62 into axial passage 16. First and second spacer drive mechanisms 44 and 66 can be configured to run off of the same power or input source in some embodiments, such that first and second spacer drive mechanisms 44 and 66, and therefore first and second retractable spacers 24 and 62, can be actuated simultaneously. First and second retractable spacers 24 and 62 can also be configured such that when both spacers 24 and 62 extend into axial passage 16, threads 58 on free electrode 42 can be received between first and second retractable spacers 24 and 62 as free electrode 42 is lowered into axial passage 16 without interference from retractable spacers 24 and 62.

In some embodiments, an electrode joining apparatus can include a plurality of retractable spacers movably connected to the electrode joining apparatus, each of the plurality of retractable spacers configured to selectively move into an axial passage of the electrode joining apparatus. One embodiment of a gear system 70 which can be incorporated into an electrode joining apparatus is shown in FIGS. 10-13. Gear system 70 can be connected to an electrode joining apparatus in a variety of orientations, and in some embodiments gear system assembly 70 can be connected between a torque device and an electrode holder. Gear system 70 can include a plurality of retractable spacers 74. In some embodiments, the plurality of retractable spacers 74 can be symmetrically distributed about gear system 70. As such, plurality of spacers 74 can apply a balanced force to a free electrode or a fixed electrode engaging plurality of spacers 74 in an axial passage of an electrode joining apparatus such that the electrodes can maintain a balanced vertical orientation within the axial passage.

Gear system 70 can include a base ring 72 to which each of the plurality of retractable spacers 74 can be pivotally connected. Each retractable spacer 74 can have a gear portion 76. Gear system 70 can include a drive gear 78 configured to mesh with each of the gear portions 76. Drive gear 78 and base ring 72 can be rotatable relative to one another. As such, drive gear 78 can cause plurality of retractable spacers 74 to rotate via gear portions 76 between a retracted position, shown in FIGS. 10-11, and an extended position, shown in FIGS. 12-13, when drive gear 78 and base ring 72 rotate relative to one another. In some embodiments, base ring 72 can be rotationally fixed to an electrode joining apparatus and drive gear 78 can be rotatably disposed on the electrode joining apparatus. Drive gear 78 can be coupled to a spacer drive mechanism 44. Spacer drive mechanism 44 can be configured to selectively rotate drive gear 78, thereby rotating each of the plurality of retractable spacers 74 on base ring 72 via gear portions 76 simultaneously between the retracted position and the extended position. In other embodiments, drive gear 78 can be rotationally fixed to an electrode joining apparatus, and base ring 72 can be rotatably disposed on the electrode joining apparatus. Base ring 72 can be coupled to a spacer drive mechanism configured to selectively rotate base ring 72 to effectively rotate plurality of retractable spacers 74 between the retracted position and the extended position.

Figure 14:
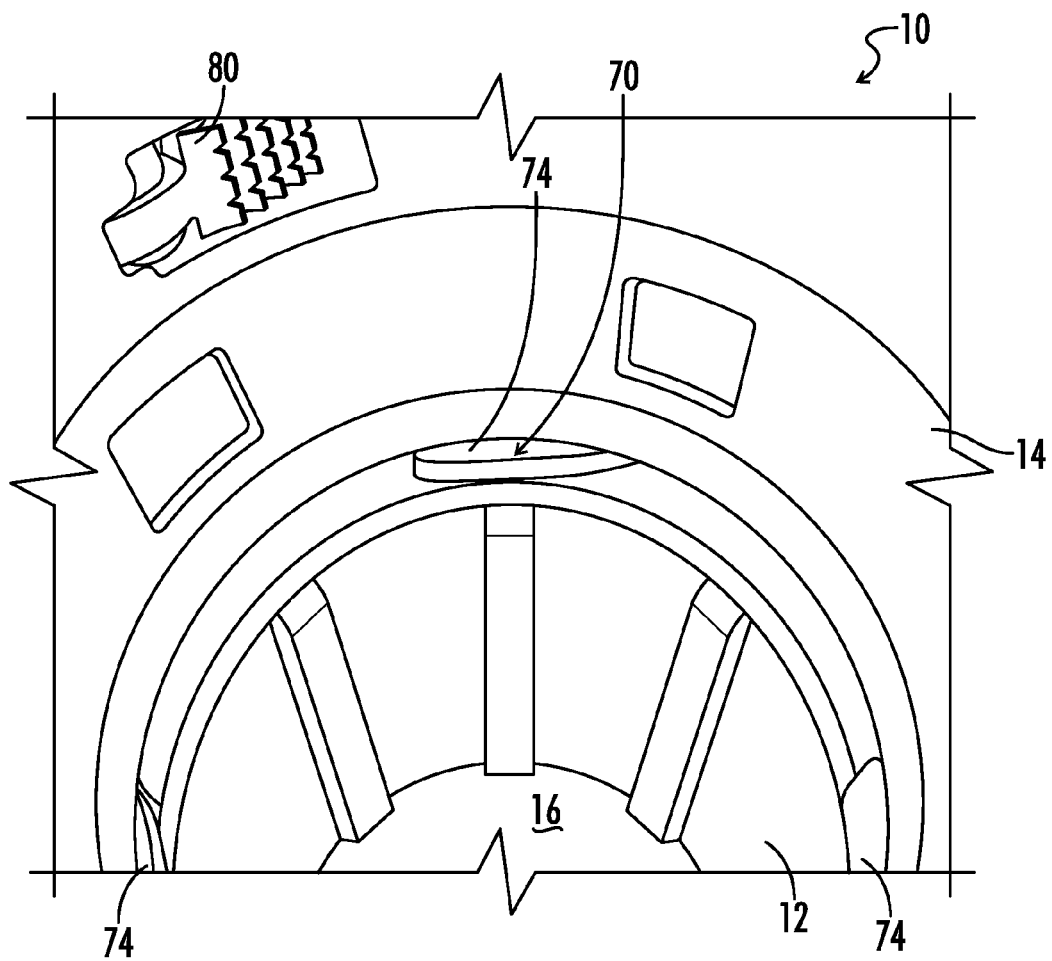
FIG. 14 is a top perspective view of an axial passage of an embodiment of an electrode joining apparatus incorporating the gear system of FIG. 10 with the retractable spacers in a retracted position.
Figure 15:
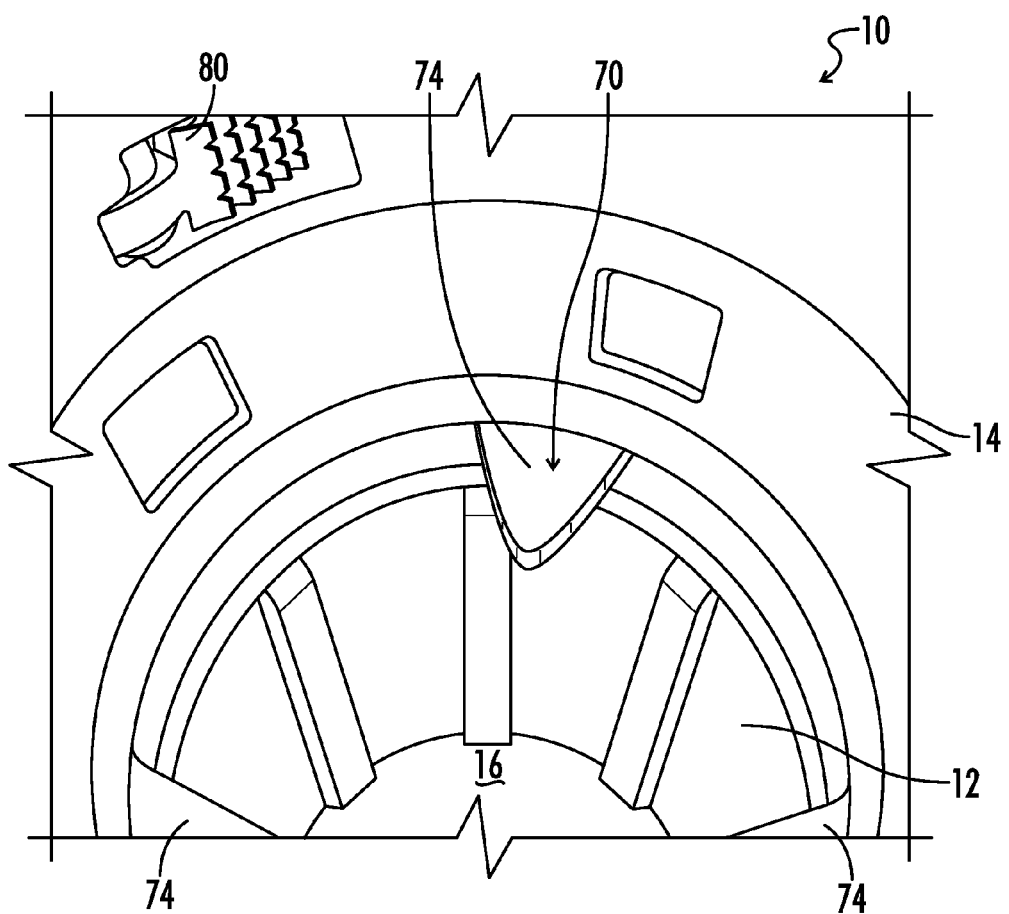
FIG. 15 is a top perspective view of the axial passage of the electrode joining apparatus of FIG. 14 with the retractable spacers in the extended position.

FIGS. 14 and 15 show a top perspective view of an axial passage 16 of an electrode joining apparatus 10 utilizing the gear system 70 of FIG. 10-13. The gear system 70 can be positioned between torque device 14 and electrode holder 12 such that plurality of retractable spacers 74 is positioned below torque device machinery and gripper pawl 80 of torque device 14. FIG. 14 shows plurality of retractable spacers 74 in a retracted position which can allow electrodes to move through axial passage 16. FIG. 15 shows plurality of retractable spacers 74 in an extended position such that a gap can be formed between a free electrode and a fixed electrode positioned in axial passage 16.

Thus, although there have been described particular embodiments of the present invention of a new and useful Electrode Joint Spacer, it is not intended that such references be construed as limitations upon the scope of this invention.

What is claimed is:

1. An electrode joining apparatus for joining a free electrode to a fixed electrode, comprising:
   an electrode holder configured to selectively hold the fixed electrode;
   a torque device positioned above the electrode holder, the torque device configured to grip and spin the free electrode to join the free electrode to the fixed electrode;
   an axial passage defined through the electrode holder and the torque device;
   a retractable spacer movably connected to the electrode joining apparatus, the retractable spacer configured to selectively move into the axial passage; and
   a spacer drive mechanism coupled to the retractable spacer, the spacer drive mechanism configured to selectively move the retractable spacer into the axial passage.

2. The apparatus of claim 1, wherein the spacer drive mechanism is a hydraulic actuator.

3. The apparatus of claim 1, wherein the spacer drive mechanism is a pneumatic actuator.

4. The apparatus of claim 1, further comprising a control console mounted to the torque device, the control console having a torque device control and an independent spacer control, the spacer control communicated with the spacer drive mechanism.

5. An electrode joining apparatus for joining a free electrode to a fixed electrode, comprising:
   an electrode holder configured to selectively hold the fixed electrode;
   a torque device positioned above the electrode holder, the torque device configured to grip and spin the free electrode to join the free electrode to the fixed electrode;
   an axial passage defined through the electrode holder and the torque device; and
   a plurality of retractable spacers movably connected to the electrode joining apparatus, each of the plurality of retractable spacers configured to selectively move into the axial passage.

6. The apparatus of claim 5, further comprising a gear system connected to the electrode joining apparatus, the plurality of retractable spacers pivotally connected to the gear system, wherein:
   the gear system includes a base ring and a drive gear rotatable relative to each other;
   each of the plurality of retractable spacers is pivotally connected to the base ring and includes a gear portion; and
   the drive gear is configured to mesh with each of the gear portions on the plurality of retractable spacers, the plurality of retractable spacers selectively moving simultaneously into the axial passage when the drive gear and the base ring rotate relative to one another.

7. The apparatus of claim 6, wherein the drive gear is rotatable relative to the base ring, and the gear system further comprises a spacer drive mechanism coupled to the drive gear, the spacer drive mechanism configured to selectively rotate the drive gear relative to the base ring.

8. An electrode joining apparatus for joining a free electrode to a fixed electrode, comprising:
   an electrode holder configured to selectively hold the fixed electrode;
   a torque device positioned above the electrode holder, the torque device configured to grip and spin the free electrode to join the free electrode to the fixed electrode;
   an axial passage defined through the electrode holder and the torque device;
   a retractable spacer movably connected to the electrode joining apparatus, the retractable spacer configured to selectively move into the axial passage; and
   a spacer support structure connected to the electrode joining apparatus, the retractable spacer movably connected to the spacer support structure.

9. An electrode joining apparatus for joining a free electrode to a fixed electrode, comprising:
   an electrode holder configured to selectively hold the fixed electrode;

a torque device positioned above the electrode holder, the torque device configured to grip and spin the free electrode to join the free electrode to the fixed electrode;

an axial passage defined through the electrode holder and the torque device;

a retractable spacer movably connected to the electrode joining apparatus, the retractable spacer configured to selectively move into the axial passage; and a lift configured to vary the vertical position of the torque device, wherein the retractable spacer is movably connected to the lift.

10. An electrode joining apparatus for joining a free electrode to a fixed electrode, comprising:

an electrode holder configured to selectively hold the fixed electrode;

a torque device positioned above the electrode holder, the torque device configured to grip and spin the free electrode to join the free electrode to the fixed electrode;

an axial passage defined through the electrode holder and the torque device;

a retractable spacer configured to selectively move into the axial passage; and a spacer drive mechanism coupled to the retractable spacer, the spacer drive mechanism configured to selectively move the retractable spacer into the axial passage.

11. The apparatus of claim 10, wherein the retractable spacer is movably connected to the electrode joining apparatus.

12. The apparatus of claim 10, wherein the spacer drive mechanism is mounted to the electrode joining apparatus.

13. The apparatus of claim 10, wherein the spacer drive mechanism is a hydraulic actuator.

14. An electrode joining apparatus for joining a free electrode to a fixed electrode, comprising:

an electrode holder configured to selectively hold the fixed electrode;

a torque device positioned above the electrode holder, the torque device configured to grip and spin the free electrode to join the free electrode to the fixed electrode;

an axial passage defined through the electrode holder and the torque device; and a retractable spacer pivotally connected to the electrode joining apparatus, the retractable spacer configured to selectively move into the axial passage.

15. The apparatus of claim 14, wherein the retractable spacer is pivotally connected to the torque device.

16. The apparatus of claim 14, wherein the retractable spacer is pivotally connected to the electrode holder.

* * * * *